United States Patent [19]

Tagaya

[11] Patent Number: 4,577,969

[45] Date of Patent: Mar. 25, 1986

[54] TESTING METHOD FOR SUBJECTS TO BE TESTED AND A DEVICE FOR SAID METHOD

[75] Inventor: Ryosaku Tagaya, Gunma, Japan

[73] Assignee: Eisai Co., Ltd., Tokyo, Japan

[21] Appl. No.: 463,107

[22] Filed: Feb. 2, 1983

[30] Foreign Application Priority Data

Jun. 3, 1982 [JP] Japan .................................. 57-94012

[51] Int. Cl.$^4$ ............................................. G01B 11/00
[52] U.S. Cl. .................................... 356/394; 356/426; 356/427
[58] Field of Search ............... 356/426, 427, 436, 441, 356/442, 434, 394, 431; 250/565

[56] References Cited

U.S. PATENT DOCUMENTS 3,777,169 12/1973 Walter et al. ......................... 250/565
3,961,898 6/1976 Neeley et al. ........................ 356/434
4,029,416 6/1977 Hawes .................................. 356/434
4,257,709 3/1981 Mostyn, Jr. .......................... 356/435

*Primary Examiner*—R. A. Rosenberger
*Assistant Examiner*—Crystal Cooper
*Attorney, Agent, or Firm*—Flynn, Thiel, Boutell & Tanis

[57] ABSTRACT

When a plural number of subjects to be tested are continuously and sequentially measured, and the values obtained by measurement are compared with a standard value for judgement, a prescribed number of newly inputted measured values are sequentially stored, a mean value is computed basing upon stored values for determining the standard value for judgement, and the measured values are compared with the standard value for judgement for judging whether these measured values are to be employed or not. Whenever new measured values are inputted, a new standard value is determined. If there is a value for an inferior subject among newly inputted measured values, the value is omitted from computation of the standard value for judgement.

7 Claims, 2 Drawing Figures

TESTING METHOD FOR SUBJECTS TO BE TESTED AND A DEVICE FOR SAID METHOD

BACKGROUND OF THE INVENTION

The present invention relates to a testing method and a testing device wherein a detection of foreign substances in a solution filled in a vessel such as an ampoule, vial and the like and a detection of the leakage or the pinhole of the vessel itself are performed with higher accuracy.

Generally, when a solution filled in a vessel which is transparent or semi-transparent is examimed, the vessel is irradiated with light, an output signal is obtained corresponding to the quantity of the light passed through the vessel, and the output signal is compared with a prescribed standard value for judging.

In the above method, the quantity of light and the wavelength of light from a projector as the light source vary as the time goes. A projector newly set and a projector whose irradiation energy is decreased after a certain period has elapsed give different output signals. Therefore, if the standard value is always set constant as ever, the judgement of the subject is not so accurate that even a good subject may be misjudged to be inferior.

For an examination of a pinhole or leak of a vessel itself such as an ampoule or vial for a solution of chemical or food, said vessel is dipped into a dense dye solution for example of methylene blue or blue dye for food, and made vacuum once, and then brought back into the normal pressure. The dense dye is introduced into the interior of the vessel through small holes, cracks and gaps which can be inspected or observed with the spectrophotometry.

In the inspection method, the degree of experience and the physical condition of an inspector influence the results of examination. Also this method is extremely inefficient.

In the spectrophotometry, the output signal is affected by changes of the projector lamp and the circuit composing element such as photodiodes, photoelectric bulb and the like of the measuring circuit system with the lapse of time and by the environmental temperature change.

Therefore, the result of measurement is changed by the characteristics of these circuit system composing elements.

Further, since the coloured solution has its absorption easily affected by the environmental temperature variation, the results of measurement is influenced by the temperature at the time of measurement leading to a phenomenon in which a good subject is misjudged to be inferior.

BRIEF SUMMARY OF THE INVENTION

The object of the present invention is to provide a testing method and a testing device which allows an accurate test without being influenced by change of light quantity of the projector lamp caused as the time goes and variation in characteristics of the measurement circuit system composing elements and subjects to be tested due to the temperature change.

As described above, the change of light quantity and wavelength of the projector lamp, and wavelength characteristic change due the temperature variation in circuit composing elements or contained solution are gradually caused as the time proceeds.

Briefly, according to the present invention, when a plural number of subjects to be tested are continuously and sequentially measured, the measured values are compared with a standard value for judgement for judging if the subject is good or not, a predetermined number of new measured values inputted are stored, a mean value is computed from the stored data for determining a standard value for judgement, and said measured values are compared with said standard value for judging subjects.

When new measured values are inputted instead of values used to compute the standard value for judgement which has already used for comparison, a new standard value is determined for newly inputted measured values.

Another object of the present invention is to make the standard value for judgement more reliable. To accomplish the objects, the computation of the mean value, the measured value which is judged to be for the inferior subject is eliminated from the data to be used as the base.

Other object of the present invention is that the method according to the invention can be used for a device employing the spectrophotometry using two wavelengths and also for the spectroscopic photometry using three wavelengths in which the influence exerted by the change of the wavelength characteristic due to the dispersion of colouring degree of the ampoule and that of the absorption caused by the temperature variation of contained solution in the coloured ampoule is decreased and when the method according to the present invention is combined with these spectrophotometric methods, a device for testing inferior subjects having a superior accuracy characteristic can be composed.

Further objects and features of the present invention will be apparent from the following description taken in connection with the accompanying drawings.

DETAILED DESCRIPTION

An embodiment of the present invention will be described hereinafter

Figure 1:
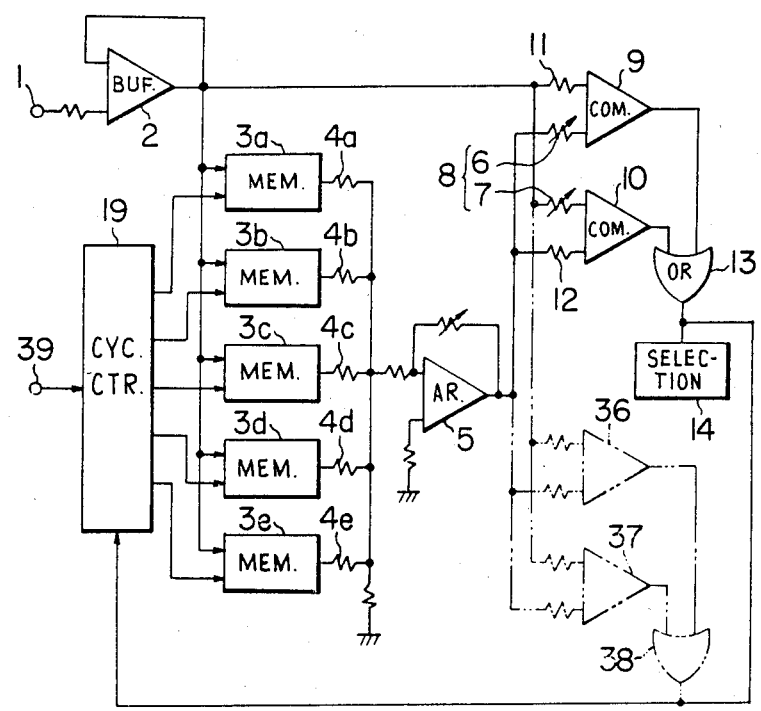
FIG. 1 is a block diagram of an embodiment of a testing method for subjects to be tested and a device for said method according to the present invention.

In FIG. 1, (1) is an input terminal. Inputted sequentially and continuously to the terminal (1) are detection signals obtained by detection of foreign substances in contained liquid which is put in a vessel such as an ampoule or vial or detection signals obtained by a test method employing a dye for detecting leakage of liquid, pinhole and the like of the vessel.

Figure 2:
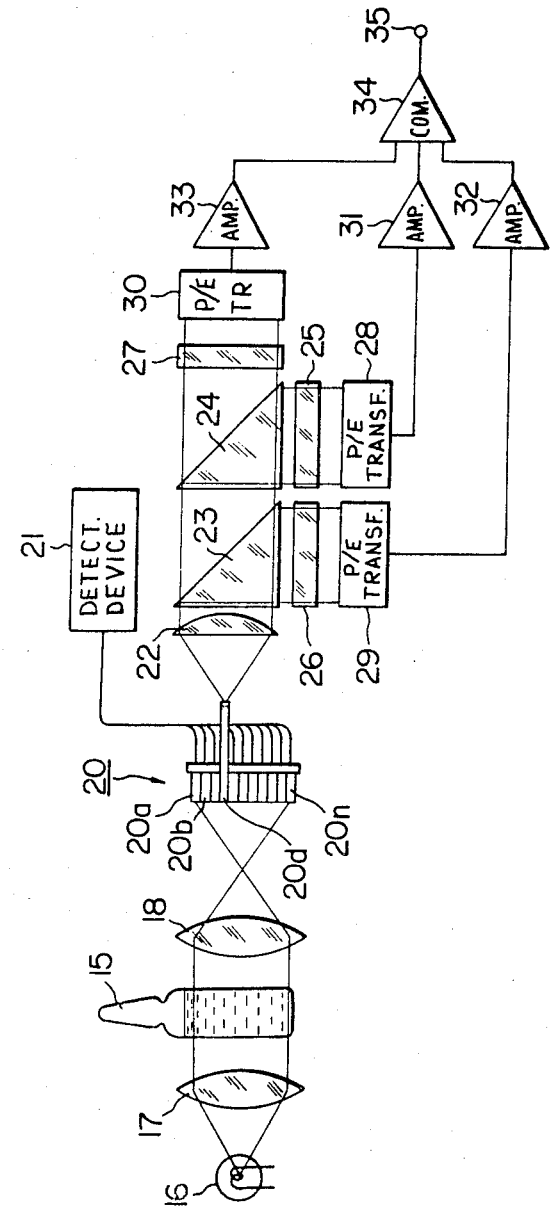
FIG. 2 is a schematic diagram of a testing device of pinholes of an ampoule as an embodiment to be connected to the input terminal of FIG. 1.

Concretely as will be described hereinafter, a detection signal for the pinhole of the vessel according to the spectrophotometry using three wavelengths as shown in FIG. 2 is inputted to the terminal (1).

Said input terminal (1) is connected to a plural number of memory circuits, more specifically to five memory circuits (3a) (3b) ... (3e). Data stored in these memory circuits are used as a base to compute an average value. Although, the memory circuits given as many as possible will do, in this embodiment five circuits is provided. A cyclecounter (19) is connected to each input of respective memory circuits. The cyclecounter (19) inputs data outputted from a buffer circuit (2) sequentially to memory circuit (3a), (3b), ... (3e), wherein the firstly outputted signal from the buffer is inputted into (3a), the secondarily outputted signal is inputted into (3b) and so forth and all the memory circuits are filled sequentially. p When all of memory circuits (3a), (3b) ... (3e) are filled, a newly outputted signal from the buffer gets into the first memory circuit (3a) replacing an old datum, the next output signal from the buffer replaces an old datum in (3b) and so forth. Thus old data in memory circuits are replaced sequentially with new data.

Outputs of said memory circuits (3a), (3b) ... (3e) are connected into one through resistors (4a), (4b) ... (4e), and then connected to an arithmetic circuit (5). Outputs of the arithmetic circuit (5) and the buffer circuit (2) are respectively connected to each one input of comparators (9) and (10) through a standard value for judgement setting member (8) composed of variable resistors (6) and (7) for setting a certain width of the sensitivity region. One of comparators, for example the comparator (9) is set by the variable resistor (6) so that it is used to set the minimum limit of a standard judging level by which the comparator (9) judges that the subject is inferior, while the comparator (10) is set by the variable resistor (7) for it to be used for the maximum limit setting. To other input side of respective comparators (9) and (10), output signals from said buffer circuit (2) and the arithmetic circuit (5) are inputted through respective resistors (11) and (12). The output side of respective comparators (9) and (10) is connected to a selection device (14) for selection of an inferior subject such as a solenoid through a gate circuit (13) composed of an OR gate. The output side of said gate circuit (13) is connected to said cyclecounter (19). When a signal which judges the subject to be inferior is outputted from the gate circuit (13), said signal controls the cyclecounter (19) not to take data from the buffer circuit (2) for computing the mean value.

In FIG. 2, a case is shown in which data to be inputted to said input terminal (1) are obtained by detecting the pinhole of the ampoule (15) by the spectrophotometry using three wavelengths.

In FIG. 2, the projector lamp (16) as light source, a objective lens (17), a focussing lens (18), and a light receiving member (20) are arranged in due order with said ampoule (15) placed between said objective lens (17) and the focussing lens (18).

Said light receiving member (20) is composed of an assembly of microlight receivers (20a), (20b), ... such as light guides divided into a plural number of small sections corresponding to the foreign substance detection limit of such glass fibre.

Each output side of respective micro-light receivers (20a), (20b), ... is connected to a detection device (21) for a foreign substance in an ampoule. A light guide for example for one bit, detecting a pinhole is introduced out from a section of microlight receivers (20a), (20b), ...

Two prismfilters, the first one (23) and the second one (24), are arranged through a condenser lens (22) at the tip of the light guide (20d). The light passing through the lens (22) is divided into three, that is the light refracted by the first filterprism, the light passing through the first prismfilter, being refracted by the second prismfilter, and the light passing through the first and the second prismfilters. These three lights have their proper wavelength range. A wavelength filter (25) selecting the characteristic wavelength of the dye bath liquid is provided for the refracted light by the second prismfilter. Standard wavelength filters (26) and (27) for comparison are respectively provided for the refracted light by the prism filter (23) and the light passing through the first and second filters. The output sides of these wavelength filters (25), (26) and (27) are connected to a comparator (34) through photoelectric transfer elements (28), (29) and (30) such as photodiodes and amplifiers (31), (32) and (33).

The output terminal (35) of the comparator (34) is coupled with the input terminal (1) in the FIG. 1.

The action of the present invention will be described. In FIG. 1, an ampoule as a subject to be examined is dipped into a dense dye solution such as methylene blue or blue dye for food, being made vacuum and then are brought back to the normal pressure. If the ampoule (15) has any pinhole, crack or gap, the dense dye solution is introduced into the ampoule (15) through it.

The ampoule (15) thus pretreated is continuously fed between the objective (17) and the focussing lens (18) by a supply device (not shown). When a high speed revolution of the ampoule once set is quickly stopped, the foreign substance in the ampoule if any will float. Any one of micro light receivers (20a), (20b), detects the foreign substance, outputting a signal of detection to the foreign substance detection device (21), then the ampoule containing the foreign substance will be eliminated.

When the ampoule (15) itself has a defect such as a pinhole and the dense dye solution is introduced into the ampoule (15), the light passing through the ampoule is coloured. The coloured light being introduced into a light guide (20d) is irradiated from the tip. The irradiated light made into parallel light flux passes through the first prismfilter (23), being refracted by the second prism filter (24), passing through the wavelength filter (25) which selects the characteristic wavelength of the dye bath.

The light flux passing through the wavelength filter (25) is then transformed into an electric signal in a photoelectric transfer element (28) and transmitted to a comparator (34) through a amplifier (31).

Other two signals for two wavelengths obtained in the same way for the standard are also transmitted to the comparator (34).

These three signals are mutually compared for the absorption or the transmittance in three wavelength regions and an analogue signal of the computed value resulted from computation is outputted.

The outputted signal from the comparator is inputted to the input terminal (1) in FIG. 1. The inputted signals are sequentially stored in memory circuits (3a), (3b) ... (3e) through the buffer circuit (2). These inputted signals into memory circuits (3a), (3b), ... are added together then divided by the number of inputs for computing a mean value. The output signal of the mean value is computed into a standard judging value having a standard judging level width with the minimum limit value and the maximum limit value. The minimum value signal is inputted to one input of the comparator (9), and the maximum value signal is inputted to one input of the comparator (10).

The measured output signals from the buffer circuit (2) are inputted to respective other inputs of comparators (9) and (10). If the inputted signal is a signal exceeding the maximum limit or a signal less than the minimum limit, any one of comparator (9) and (10) outputs a detection signal of pinhole and when a signal is within the standard judging level width, it is not outputted. The outputs from comparators (9) and (10) become a output signal for judgement in the gate (13) operating a selection device for eliminating the inferior subject. When a signal which judged a subject to be inferior is outputted from the gate circuit (13), the cycle counter (19) controls memory circuit (3a), (3b) . . . (3e) not to input the measured output signal which measured the inferior subject.

That is, the measured output signal for an inferior subject is far over or below a certain standard value, and such signal may extremely raise or lower the mean value and make the accuracy of judgement lower, therefore, such signal is eliminated from the computation of the mean value. When the level for the standard judgement value and the level width to be eliminated from the computation of the mean value are to be separately set, the output signal for judgement from the gate circuit (13) may be not inputted but a different level width set by comparators (36) and (37) provided, otherwise as shown in a chain line in FIG. 1 may be compared with the measured value, and a resultant output signal may be inputted to the cyclecounter (19) through a gate circuit (38) composed of an OR gate.

For controlling the timing of switch-over of memory circuits (3a), (3b), . . . (3e), a signal which checks if there is a vessel from a device for supplying ampoules or not is inputted at 39 to the cycle counter (19). Once the output signal for judgement from the gate circuit is inputted and the judgement is performed, succeeding new measured output signal is inputted to a memory circuit for replacing the oldest datum existing in memory circuits to compute a new mean value. The composition of the memory circuit group composed of such memory circuits (3a), (3b) . . . (3e), the cycle counter (19) and the arithmetic circuit (5) will do as it is, however, for treating a number of signals, the treatment by a micro-computer using the digital value transformed from the analogue value is made easy and the composition of the circuit group is made simple. The variation of the mean value is made decreased by increasing the number of memory circuits.

However, as described above, when a circuit is introduced which refuses a inferior signal, even the minimum number of memory circuits can provide increased accuracy of mean value.

What is claimed is:

1. A testing method for testing a plural number of subjects comprising: sequentially and continuously measuring said subjects to obtain measured values, storing in plural respective memory circuits sequentially obtained ones of a plural number of said measured values as they are sequentially obtained, computing a mean value of the stored measured values, determining a standard value for judgement from said mean value, comparing the next obtained measured value with said standard value for judgement for judging, then using said next obtained measured value to replace one of the measured values stored in a said memory circuit, said mean value being computed after each such replacement is made, and repeating the foregoing steps to update said memory circuits and thereby vary said mean value and said standard value for judgement in correspondence to variation of subsequent measured values.

2. The method of claim 1 in which said standard value for judging is the limits on an acceptable range about said mean value, and including the step of preventing inclusion in said mean value of a next obtained measured value which lies outside said acceptable range.

3. A testing device for vessels to be tested, comprising means for applying a light flux to successive vessels and a light receiving member of a light detector receiving light therefrom, said vessels being supplied sequentially and continuously and being tested by the variation of light received by the light receiving member to provide corresponding output signals from the latter, a group of memory circuits respectively storing sequentially an individually measured one of said output signals, an arithmetic circuit connected to said group of memory circuits for computing the mean value of the stored signals, means for setting a standard value for judgement by providing a certain fixed sensitivity width to the mean value obtained by the arithmetic circuit, a comparator for comparing the standard value for judgement with the next individual measured output signal obtained from said light receiving member, said standard value setting means connecting the mean value output of said arithmetic circuit to said comparator and a selection device responsive to the comparator output for indicating a faulty vessel.

4. A testing device according to claim 3 wherein said memory circuits have inputs connected in parallel to an output path from said light receiving member, and including a cyclecounter having plural enabling outputs repectively connected to said memory circuits for causing the memory circuit then containing the oldest data to receive new data when an output signal from the light receiving member appears at said parallel inputs of said memory circuits.

5. A testing device according to claim 3 wherein said sensitivity width corresponds to a minimum limit judging standard value and a maximum limit judging standard value, and first and second said comparators are provided, each comparator comparing an output signal from said light receiving member with one or the other of the minimum and maximum limit judging standard values.

6. A testing device according to claim 3 including a cyclecounter for controlling storing of output signals from the light receiving member in the memory circuits, and means fed by the comparator and having its output connecting to the selection device and to the cyclecounter and causing the latter not to store a specific output signal from said light receiving member in the group of memory circuits.

7. A testing device according to claim 3 comprising a cyclecounter for enabling storing in said memory circuits selectively, said means for setting a standard value for judgement comprising a setting member responsive to the computed mean value at the output side of the arithmetic circuit for setting said sensitivity width, a further comparator, the first mentioned and further comparators being connected for comparing respective maximum and minimum limits of said sensitivity width with the measured output signal from the light receiving member, an OR gate having inputs connected to the first mentioned and further comparators for controlling the cyclecounter with the output of the OR gate to prevent a specific measured output signal from being inputted to the group of memory circuits when said specific measured output signal is less than said minimum limit or greater than said maximum limit.

* * * * *